(12) United States Patent
Tomita

(10) Patent No.: US 6,231,523 B1
(45) Date of Patent: May 15, 2001

(54) PAIN INFORMATION DETECTING DEVICE

(76) Inventor: Mitsuei Tomita, 109-407, Yamanote-cho, Naka-ku, Yokohama-shi 231-0862 (JP)

(*) Notice: Subject to any disclaimer, the term of this patent is extended or adjusted under 35 U.S.C. 154(b) by 0 days.

(21) Appl. No.: 09/581,482

(22) PCT Filed: Nov. 12, 1999

(86) PCT No.: PCT/JP99/06354

§ 371 Date: Jun. 14, 2000

§ 102(e) Date: Jun. 14, 2000

(51) Int. Cl.[7] .................................................. A61B 5/00
(52) U.S. Cl. .......................... 600/586; 600/485; 600/400; 600/493
(58) Field of Search .................... 600/485–490, 600/453–456, 586

(56) References Cited

U.S. PATENT DOCUMENTS

| 5,012,817 | 5/1991 | Zeilinski et al. | 128/744 |
|---|---|---|---|
| 5,095,912 | 3/1992 | Tomita | 128/672 |
| 5,301,675 | 4/1994 | Tomita | 128/672 |
| 5,316,005 | 5/1994 | Tomita | 128/680 |
| 5,388,585 | 2/1995 | Tomita | 128/680 |
| 5,406,954 | 4/1995 | Tomita | 128/680 |
| 5,423,324 | 6/1995 | Tomita | 128/680 |
| 5,651,369 | 7/1997 | Tomita | 128/680 |
| 5,724,980 | * 3/1998 | Nakamura et al. | 600/484 |

FOREIGN PATENT DOCUMENTS 0630608   12/1994   (EP) .

* cited by examiner

Primary Examiner—Robert L. Nasser
(74) Attorney, Agent, or Firm—Ladas & Parry

(57) ABSTRACT

A cuff (200), having a blood shutting bag (210) and a detection bag (220), is attached to an upper arm of a patient and a main device unit (100) is made to operate. A CPU (130) performs the measurement operation in accordance with a program inside a memory (160). First, the air pump (140) is started to deliver air to the respective bags, the cuff pressure is set higher than the systolic pressure, and after the blood flow at the upper arm has been stopped completely, a leak valve (150) is gradually opened to lower the cuff pressure. During the lowering of pressure, the Korotkoff sound that is generated at the detection bag (220) is detected by a sound wave sensor (110) and is taken as digital data into the memory (160). This Korotkoff sound is Fourier transformed and the result thereof is displayed as a spectral waveform on a display device (170) and printed out by means of a printer (180). The spectral waveform that is obtained contains information on pain at specific locations that are determined according to the cuff pressure at which the Korotkoff sound was sampled and can be used for diagnosis.

6 Claims, 10 Drawing Sheets

PAIN INFORMATION DETECTING DEVICE

TECHNICAL FIELD

The present invention relates to a pain information detecting device and, more particularly, to a detecting device to obtain information on pain which a patient is suffering, in a form of electrical signals by using a cuff attached onto the upper arm of the patient.

BACKGROUND ART

In the field of medicine, various detecting devices and measuring devices are used to recognize the various phenomena that occur in the body of a patient as objective data. For example, blood pressure measurement is a most readily used measuring means and blood pressure measurement devices, etc. for general household use are commercially available. Normally, a medical practitioner obtains information on subjective symptoms from the chief complaints of a patient or by inquiry of the patient him/herself, collects objective information using various detecting devices and measuring devices, and provides a final diagnosis upon comprehensive examination of such information.

Pain is the most significant symptom among the subjective symptoms of the patient him/herself and a majority of patients complain of pain in initial diagnosis inquiries. A medical practitioner asks the patient questions on such matters as where the pain is, what sort of pain is being felt, etc. and specifies the location of pain and the type of pain. However, information on pain obtained by such inquiries is only obtained through verbal expressions of pain that is felt subjectively by the patient and cannot be regarded as objective data. In many years, research on the measurement of pain as objective data has been carried out in various fields. The pain signal is considered to be an electrical signal that is transmitted in the internal nervous system. For example, a conventional device was developed which uses a bridge circuit to detect the minute electric currents that flow through a needle inserted near a nerve so that pain felt by patients is obtained as an electrical signal. However, since a needle must be inserted into a portion where the patient is complaining of pain, such a device has not yet become practical for clinical use.

The object of the present invention is therefore to provide a pain information detecting device with which information concerning pain can be obtained in the form of electrical signals by a simple method.

DISCLOSURE OF INVENTION

This invention is based on the concept that information concerning pain is contained in the waves that propagate through an artery. Arteries play the role of transfer pipes for blood that circulates throughout the body and comprises a circulatory network that is laid across the body, from the heart to the peripheral parts. The various physical data that can be obtained from an artery are thus considered to contain valuable information concerning the entire body. For example, blood pressure value, which is a representative example, is normally measured at the upper arm and provides important physical information concerning the entire body. The present inventor, through measurements of the Korotkoff sound, which is generated as blood passes through an artery under compression, of numerous patients, has come to find that there is a correlation between pain and the Korotkoff sound waveform. In particular, the inventor has found that when Fourier transform is applied to the Korotkoff sound signal, the information on pain can be expressed in a visually recognizable form and that pain information can thus be detected by a simple method.

With the first mode of this invention, a pain information detecting device is comprised of a cuff, having a blood flow shutting bag for stopping the blood flow in an artery, a pressure control device for controlling the pressure of this blood flow shutting bag, a sound wave sensor, which detects the Korotkoff sound that arises when blood flows through the artery under compression by the blood flow shutting bag, and a computation device, which Fourier transforms the Korotkoff sound signal detected by the sound wave sensor, and the cuff is attached onto the upper arm of a patient to enable information on the pain felt by the patient to be indicated in an objective manner.

With the second mode of this invention, the above-described pain information detecting device of the first mode has a detection bag, which is partially interconnected with the blood flow shutting bag and is smaller in volume than the blood flow shutting bag, provided at the cuff to enable the sound wave sensor to detect the Korotkoff sound based on the pressure fluctuation inside the detection bag and thereby improve the detection sensitivity of the Korotkoff sound.

With the third mode of this invention, the pain information is indicated by cutting off components of a prescribed frequency or higher after Fourier transformation in the above-described pain information detection of the first mode or second mode to enable the indication of noise components to be restricted.

With the fourth mode of this invention, the Fourier transform results are indicated in the form of a spectral waveform or a histogram in the above-described pain information detecting device of the first to third modes to enable visual ascertainment of the pain information to be performed readily.

With the fifth mode of this invention, the above-described pain information detecting device of the first to fourth modes is provided with a pressure control device, which controls the pressure of the blood flow shutting bag to decrease gradually from a pressure that is adequately high for shutting the blood flow to enable indication of the Fourier transform results of the respective Korotkoff sounds detected at a plurality of pressures.

With the sixth mode of this invention, the apparent correlation is utilized between the pressures of the blood flow shutting bag during Korotkoff sound detection and the positions of various parts of the body. The Fourier transform results of the respective Korotkoff sounds detected at a plurality of pressures with the above-described pain information detecting device of the fifth mode are indicated in correspondence to the respective, specific parts of the body.

BEST MODE FOR CARRYING OUT THE INVENTION

§ 1 Basic Arrangement of the Device

Figure 1:
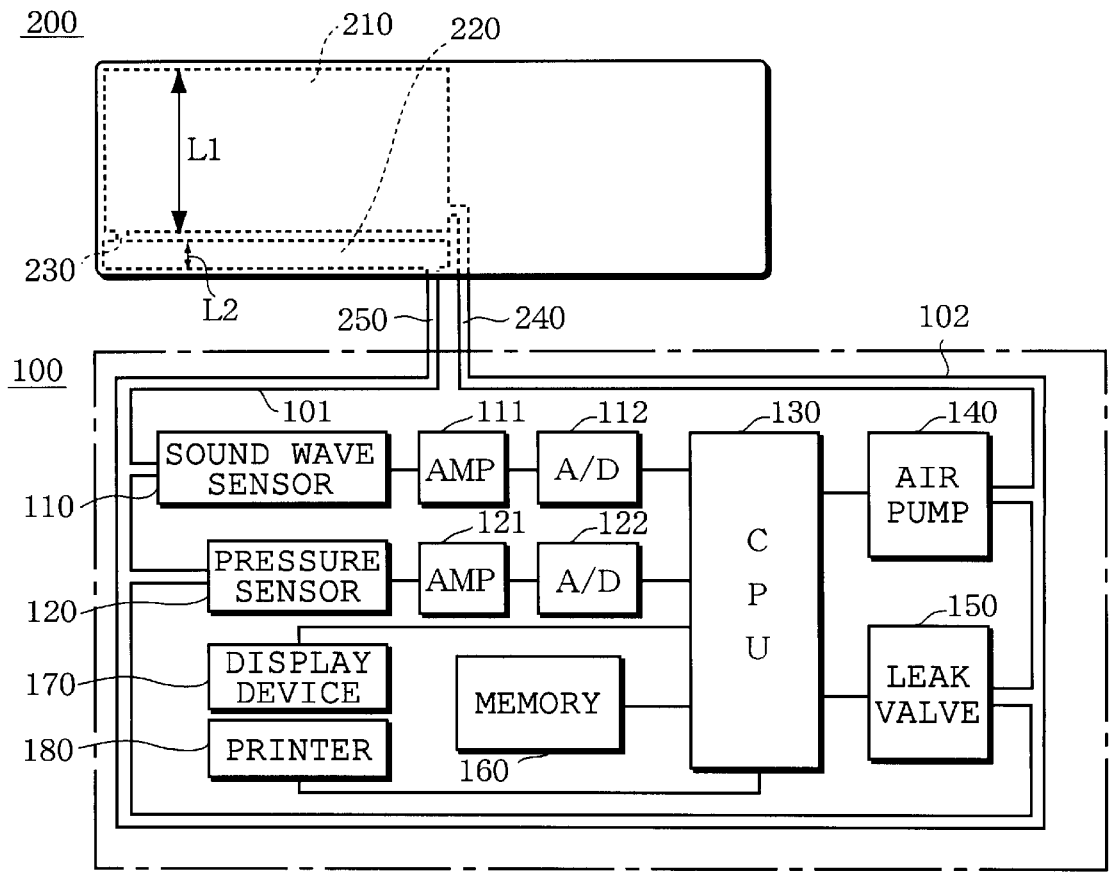
FIG. 1 is a block diagram (the portion of the cuff being a plan diagram) which shows the basic arrangement of a pain information detecting device of an embodiment of this invention.

FIG. 1 shows the basic arrangement of a pain information detecting device according to an embodiment of this invention. This device is mainly comprised of the two components of a main device unit 100 (surrounded by alternate long and short dash lines) and a cuff 200. Cuff 200 has a blood flow shutting bag 210 and a detection bag 220, which is smaller in volume than blood flow shutting bag 210, and blood flow shutting bag 210 and detection bag 220 are interconnected with each other by a connection path 230. Blood flow shutting bag 210 has a size necessary for shutting the blood flow of the artery of the upper arm, and with the present embodiment, the length L1 in the Figure is approximately 12 cm. Meanwhile, detection bag 220 has a size suitable for the detection of Korotkoff sounds, and with this embodiment, the length L2 in the Figure is approximately 2 cm. A duct 240, for passage of air, extends from blood flow shutting bag 210 to the exterior, and likewise, a duct 250 extends from detection bag 220 to the exterior. This cuff 200 is used upon attachment to the upper arm in the orientation shown in FIG. 2.

Meanwhile, the main device unit 100 has the following arrangement. First, a sound wave sensor 110 and a pressure sensor 120 are provided in a pipe 101, which is connected to duct 250. Though both of these sensors are, in principle, sensors that detect the pressure inside detection bag 220 via duct 250, whereas pressure sensor 120 is a sensor that is suited for measuring the pressure value itself, sound wave sensor 110 is a sensor that is suited for the detection of pressure fluctuations within the frequency bandwidth of sound waves and especially for the detection of pressure fluctuations within the frequency bandwidth of Korotkoff sounds. The analog signals detected by sound wave sensor 110 are amplified by an amplifier 111, converted into digital signals by an A/D converter 112, and input into a CPU 130. Likewise, the analog signals detected by pressure sensor 120 are amplified by amplifier 121, converted into digital signals by an A/D converter 122, and input into CPU 130. An air pump 140 and a leak valve 150 are connected to a pipe 102, which in turn is connected to duct 240. This air pump 140 and leak valve 150 are controlled by CPU 130. Pipe 101 and pipe 102 are interconnected and blood flow shutting bag 210 and detection bag 220 are interconnected by connection path 230. Blood flow shutting bag 210 and detection bag 220 are thus inherently maintained at the same pressure. However, since blood flow shutting bag 210 is large in volume, the Korotkoff sounds that arise in blood flow shutting bag 210 tend to become distorted in waveform. Sound wave sensor 110 is therefore preferably connected as close to duct 250 as possible as shown in the illustrated example so as to detect mainly the Korotkoff sounds that arise in detection bag 220.

Memory 160 has a region for storing the program to be executed by CPU 130 and the data obtained by execution of this program. CPU 130 executes the below-described operation procedure based on the program inside memory 160 and stores the data obtained as a result in memory 160. CPU 130 is also connected to a display device 170 for display of the detection results and a printer 180 for printout of the detection results.

§ 2 Basic Operation of the Device

Figure 2:
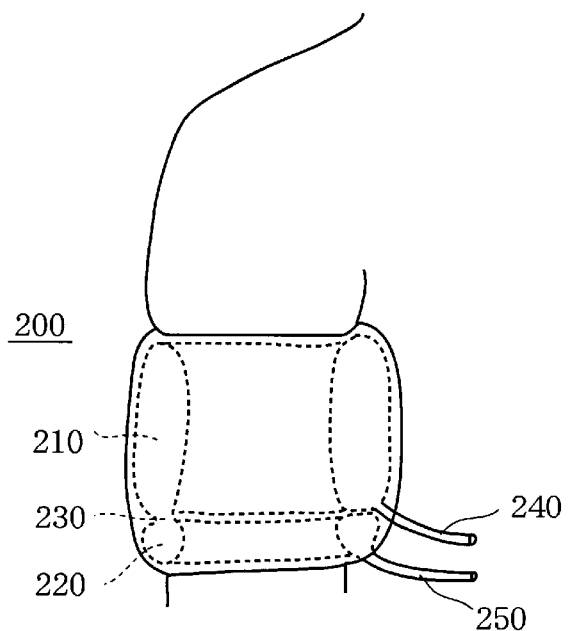
FIG. 2 is a diagram which shows the condition where the cuff of the detecting device shown in FIG. 1 is attached to an upper arm.

The basic procedure of the pain information detecting operation using the device of FIG. 1 shall now be described. As shown in FIG. 2, cuff 200 is attached to the upper arm of a patient. For efficient detection of the Korotkoff sounds by detection bag 220, the cuff is preferably attached so that blood flow shutting bag 210 will lie at the upstream side of the artery of the upper arm and detection bag 220 will lie at the downstream side as illustrated. When the measurement starting switch (not shown) provided at the main device unit 100 is then pressed, CPU 130 executes a series of measurement operations based on the program inside memory 160. Here, this measurement operation procedure shall be described using the graph of FIG. 3.

Figure 3:
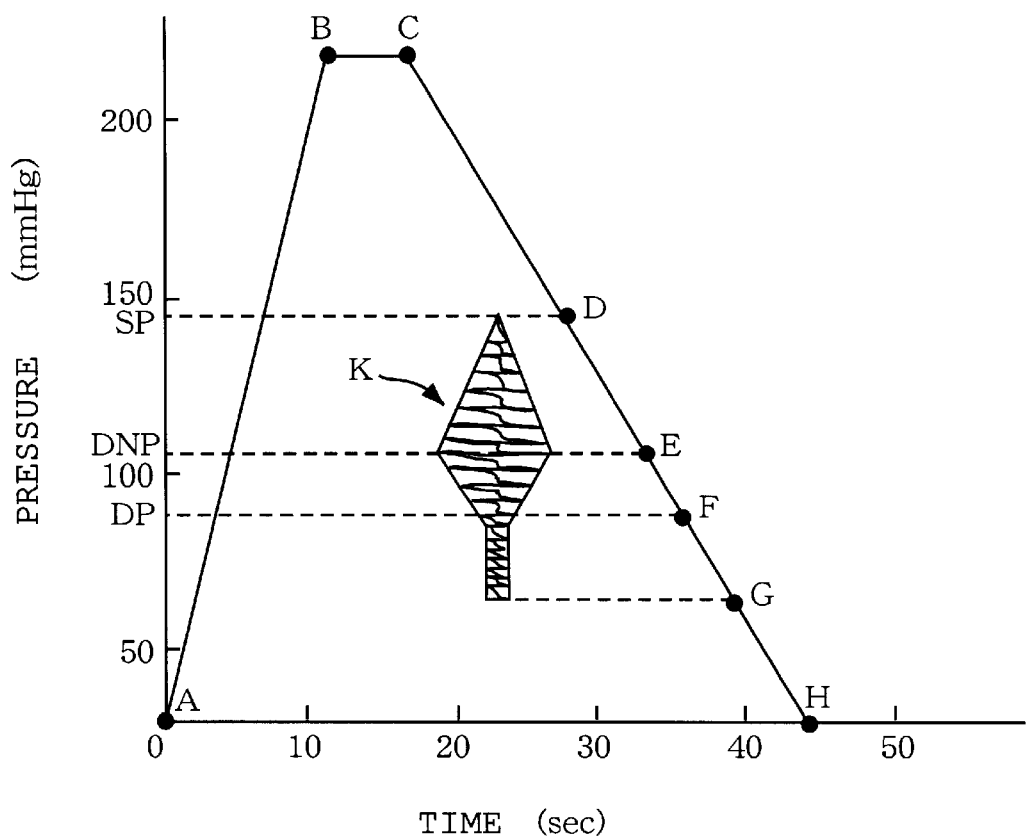
FIG. 3 is a graph which shows the operating procedure of the detecting device shown in FIG. 1.

An important procedure in this measurement operation is the pressure control procedure. As has been mentioned above, this detecting device has an air pump 140 and a leak valve 150 which enable control of the pressure of blood flow shutting bag 210 and detection bag 220. That is, if the pressure is to be increased, air pump 140 is made to operate and deliver air into the bag, while if the pressure is to be decreased, leak valve 150 is opened to allow the air inside the bag to leak out. The graph of FIG. 3 shows the variation of the pressure inside the bags after the start of measurement, and CPU 130 performs the operation of providing prescribed control signals to air pump 140 and leak valve 150 so that the pressure inside the bags will vary as shown in the graph.

Figure 4:
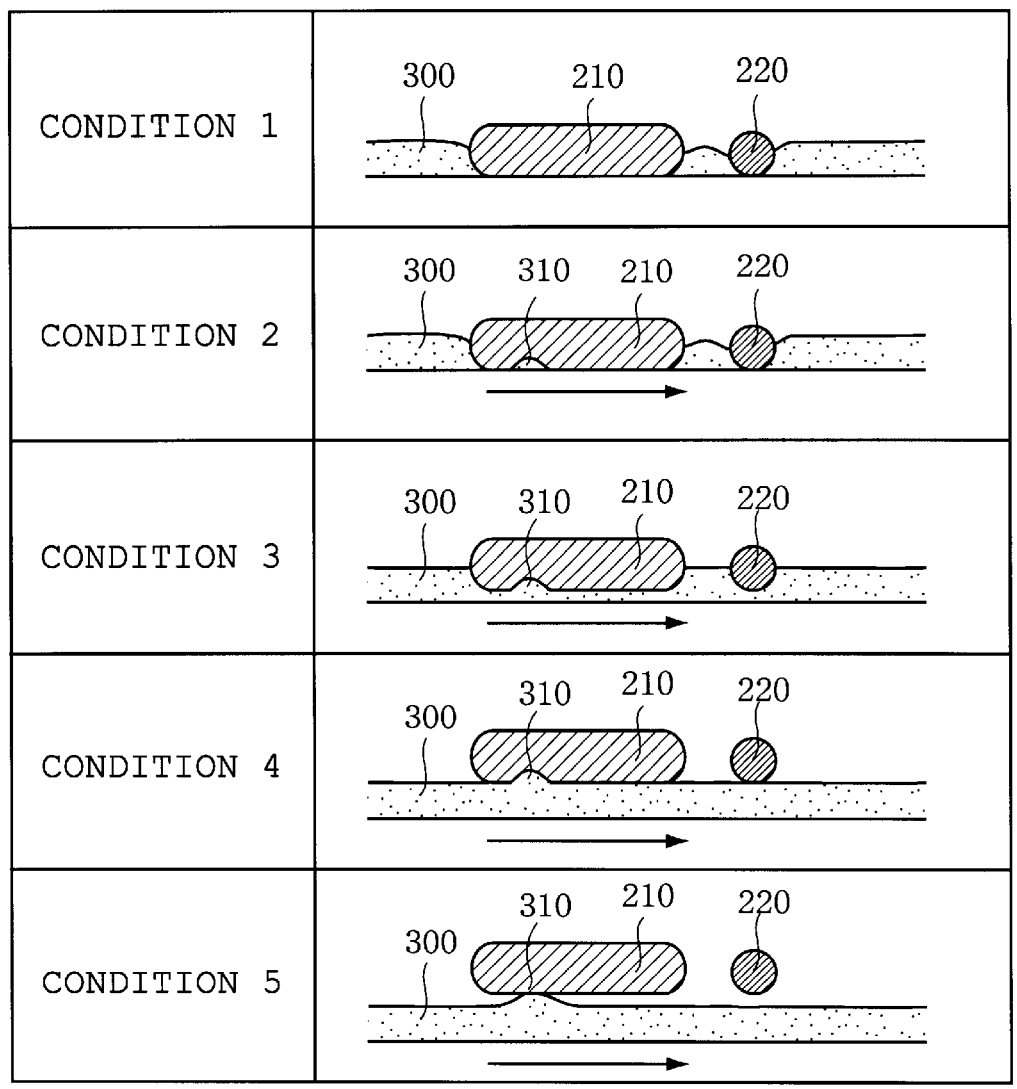
FIG. 4 is a sectional view which shows the relationship between the cuff and an artery during the detection operation by the detecting device shown in FIG. 1.

When the measurement is started, CPU 130 first starts up air pump 140 to deliver air into the bags and thereby gradually increase the pressure. Blood flow shutting bag 210 then gradually compresses the artery and its internal pressure eventually reaches the pressure at which the blood flow is stopped completely (points A to B of the graph). The relationship between cuff 200 (blood flow shutting bag 210 and detection bag 220) and the artery 300 at this time is shown in the sectional view of condition 1 of FIG. 4. In FIG. 4, the heart lies to the left side of the Figure, the periphery lies to the right side of the Figure, and blood flows inside artery 300 from the left side to the right side of the Figure as a pulse wave synchronized with the beating of the heart. However in condition 1, since the pressure inside blood flow shutting bag 210 is high, the blood flow is completely shut off. Here, this pressure value is maintained for some time (points B to C) to check for any leakage of air from the respective bags. If an air leak is found at this point, leak valve 150 is rapidly opened fully to discharge the air, the measurement operation is stopped, and the occurrence of abnormality is notified.

If an air leak is not found, it is deemed that there are no abnormalities and the normal measurement operation begins. That is, CPU 130 controls the gradual opening of leak valve 150 to gradually decrease the pressure. When the pressure corresponding to point D of the graph of FIG. 3 is reached, Korotkoff sound is generated. The waveform K in the graph indicates the amplitudes of the Korotkoff sounds obtained in correspondence to the respective pressure values when the pressure is reduced gradually from point D. Korotkoff sounds are generated when the point D is passed since a portion 310 of the blood begins to flow past blood flow shutting bag 210 against the pressure of blood flow shutting bag 210 as illustrated in condition 2 of FIG. 4. The pressure corresponding to point D is at a pressure known as systolic pressure SP. When the pressure is gradually decreased further from point D, the amount of blood that flows increases and the amplitude of the Korotkoff sound also increases gradually. And at point E in the graph of FIG. 3, the amplitude of the Korotkoff sound takes on the maximum value. The pressure at this point is known as dicrotic notch pressure DNP. When the pressure of blood flow shutting bag 210 is decreased further, the closed artery 300 becomes gradually released as shown by condition 3 of FIG. 4, and since resistance against blood flow thus decreases, the amplitude of the Korotkoff sound also decreases gradually. And when the point F is passed, the Korotkoff sound will be substantially constant in amplitude even when the pressure is lowered further. The pressure corresponding to this point F is known as diastolic pressure DP, and as shown by the condition 4 in FIG. 4, corresponds to the static pressure of artery 300. When the pressure is decreased further (points F to G), cuff 200 will become lifted with respect to artery 300 as shown by condition 5 of FIG. 4, and when the pressure is decreased further from point G, the Korotkoff sound disappears and point H is eventually reached.

The series of measurement operations is as described above. These measurement operations are similar to the blood pressure measurement operations of a general blood pressure manometer. That is, in blood pressure measurement operations, the systolic pressure SP (point D), at which the Korotkoff sound is generated, and the diastolic pressure DP (point F), at which the Korotkoff sound becomes small, are determined. In the pain information detecting device of the present invention, the waveform of the Korotkoff sound K itself is taken in as data. That is, the waveforms of the Korotkoff sounds that are generated in the pressure range of points D to G of the graph of FIG. 3 are taken into CPU 130 from sound wave sensor 110 and stored as data in memory 160. That Korotkoff sound is generated when blood flows through an artery under compression has been known for ninety years. However, clinically, this Korotkoff sound has only been used as information for determining the systolic pressure SP (point D) and the diastolic pressure DP (point F) with a blood pressure manometer. A major characteristic of the present invention is that the waveform data of the Korotkoff sound, which has priorly been used only as blood pressure information, are handled as important data that contain pain information. Since the systolic pressure SP (point D) and the diastolic pressure DP (point F) are determined by the above-described measurement operations, the device of this embodiment also has the functions of a general blood pressure manometer.

Figure 5:
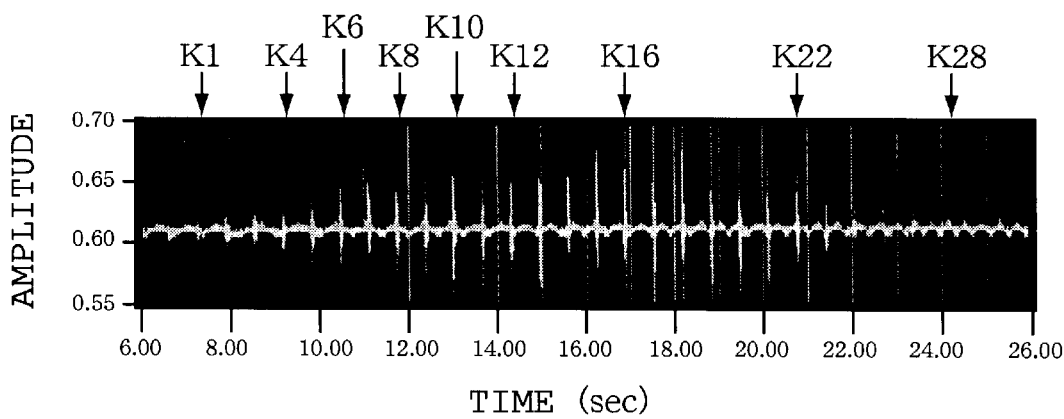
FIG. 5 is a graph which shows a Korotkoff sound waveform detected by the detecting device shown in FIG. 1.

As illustrated by waveform diagram K in FIG. 3, the Korotkoff sound has a waveform that appears in synchronized timing with the heartbeat in the pressure range of points D to G of the graph. FIG. 5 is a graph that shows an example of a Korotkoff sound waveform which has actually been measured by the detecting device of this embodiment. While the abscissa of the Figure is the time axis (sec), this time axis corresponds to the pressure axis within the pressure range of points D to G of the graph of FIG. 3. In other words, the left end of the graph shown in FIG. 5 corresponds to point D and the right end corresponds to point G. Thus when the above-described series of the measurement operations is executed, data indicating the respective Korotkoff sound waveforms detected at a plurality of pressures are obtained in memory 160. In the graph of FIG. 5, the pulse-form waveforms that appear repeatedly at a period of approximately 0.7 sec (period of the heartbeat) are the individual Korotkoff sound waveforms, and the waveforms to the left side of the Figure are those that are detected at higher pressures. For the sake of convenience, the detected waveforms shall be referred to in numbered manner as first waveform K1, second waveform K2, third waveform K3, etc. in the order starting from the waveform detected at high pressure (systolic pressure SP).

Along with performing the above-described pressure control operation, CPU 130 performs the process of Fourier transforming the respective Korotkoff sounds obtained in memory 160. This process can be performed by calculations based on a fast Fourier transform (FFT) program prepared inside memory 160. This Fourier transform is performed separately and independently on each individual Korotkoff sound waveform, i.e. first waveform K1, second waveform K2, third waveform K3, etc. The Fourier transform results that are thus obtained are displayed on the screen by display device 170 and are printed out on paper as necessary by means of printer 180. As has been mentioned above, these Fourier transform results become data that objectively indicate the pain information of a patient. Since noise components are contained in an actual Korotkoff sound waveform, it is preferable to indicate the Fourier transform data by cutting the higher frequency components off than a prescribed cutoff frequency. With the device of this embodiment, components of 150 Hz or higher, which are contained in the acoustic waveform taken in as Korotkoff sound, are deemed to be noise components, and the Fourier transform results are indicated with the frequency components less than 150 Hz.

§ 3 Specific Examples of Detection by the Device of the Invention

Specific examples of detection using the above-described detecting device of the embodiment shall now be described. These detection examples are the results of measurements made on a patient with a disorder in the shoulder joint. When this patient raises the right arm above the horizontal level, the patient complains subjectively of having symptoms of severe pain in the right shoulder. Measurements with the detecting device of the present embodiment were thus made in two conditions where the right arm is dropped to the side (condition of no pain) and where the right arm is raised higher than the horizontal level (condition of pain). That is, cuff 200 was attached to the right upper arm, the above-described series of measurement operations were performed in the "no-pain" condition in which the right arm is dropped to the side, and then the above-described series of measurement operations were performed in the "pain" condition in which the right arm is raised above the horizontal level. A part of the results is shown in FIG. 6 to FIG. 13.

Figure 6:
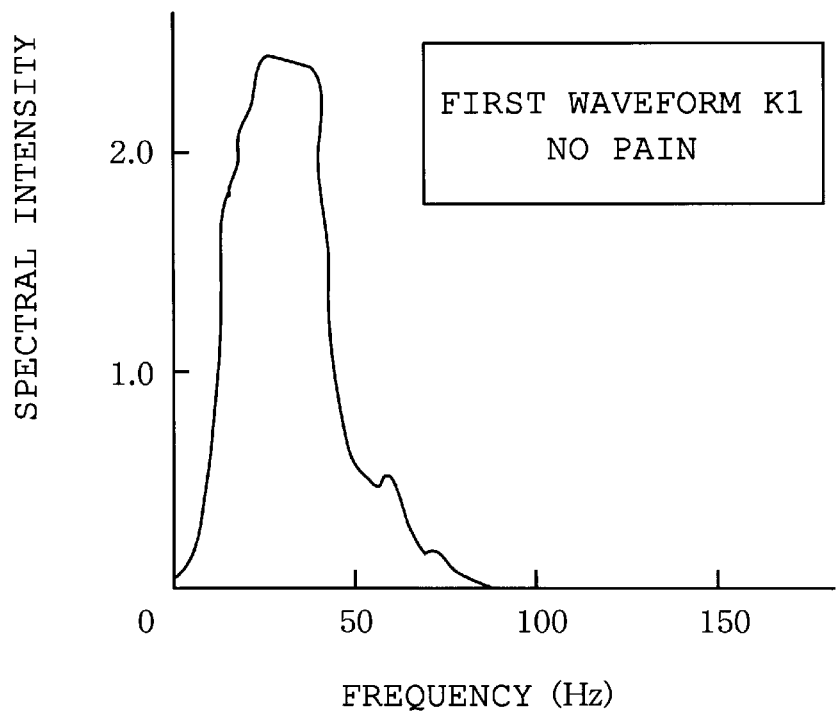
FIG. 6 is a graph which shows the Fourier transform spectrum of the first Korotkoff sound waveform in a condition where a specific patient feels no pain.
Figure 7:
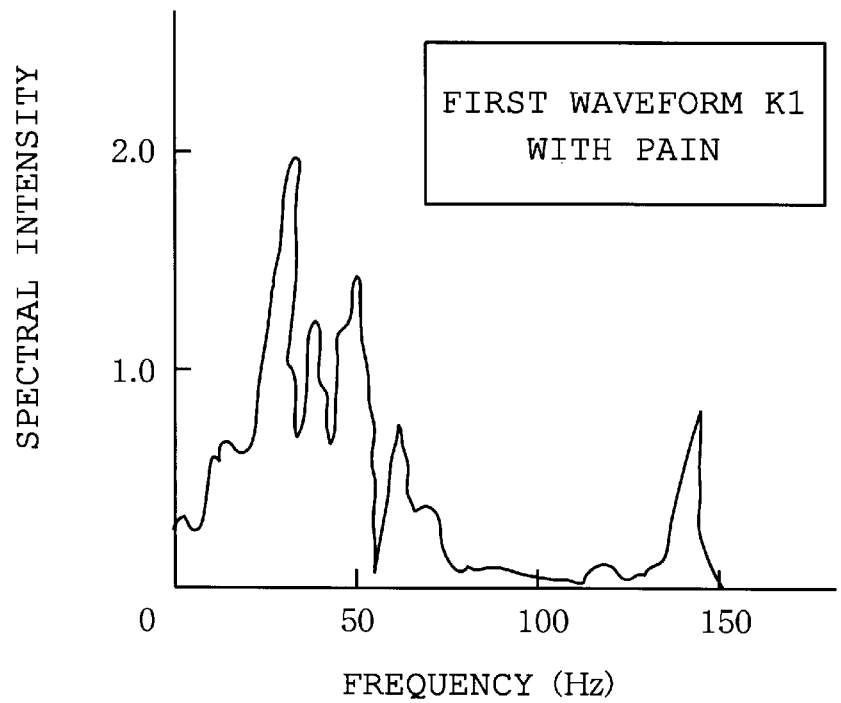
FIG. 7 is a graph which shows the Fourier transform spectrum of the first Korotkoff sound waveform in a condition where the specific patient feels pain.
Figure 8:
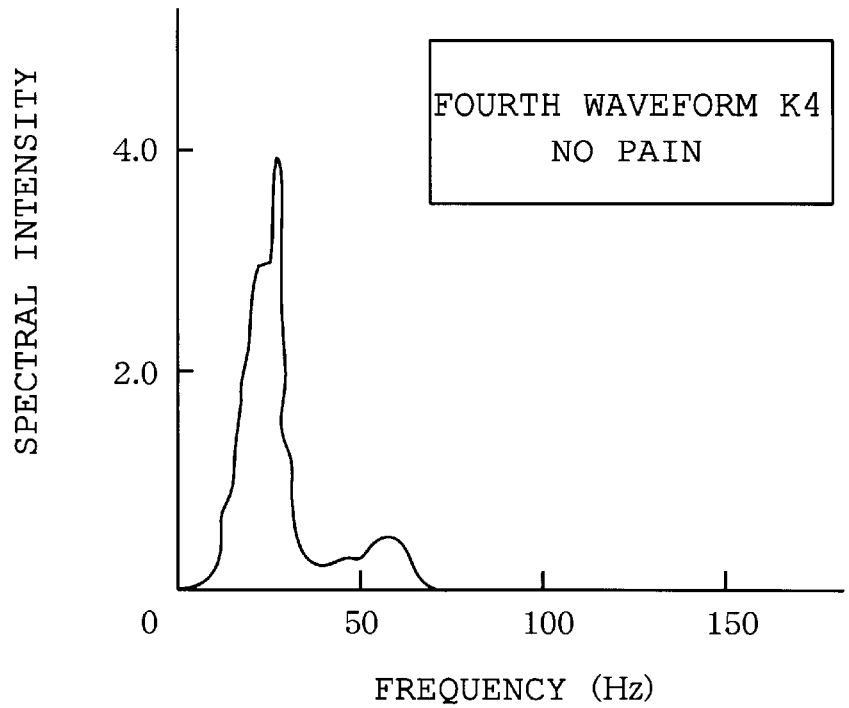
FIG. 8 is a graph which shows the Fourier transform spectrum of the fourth Korotkoff sound waveform in a condition where the specific patient feels no pain.
Figure 9:
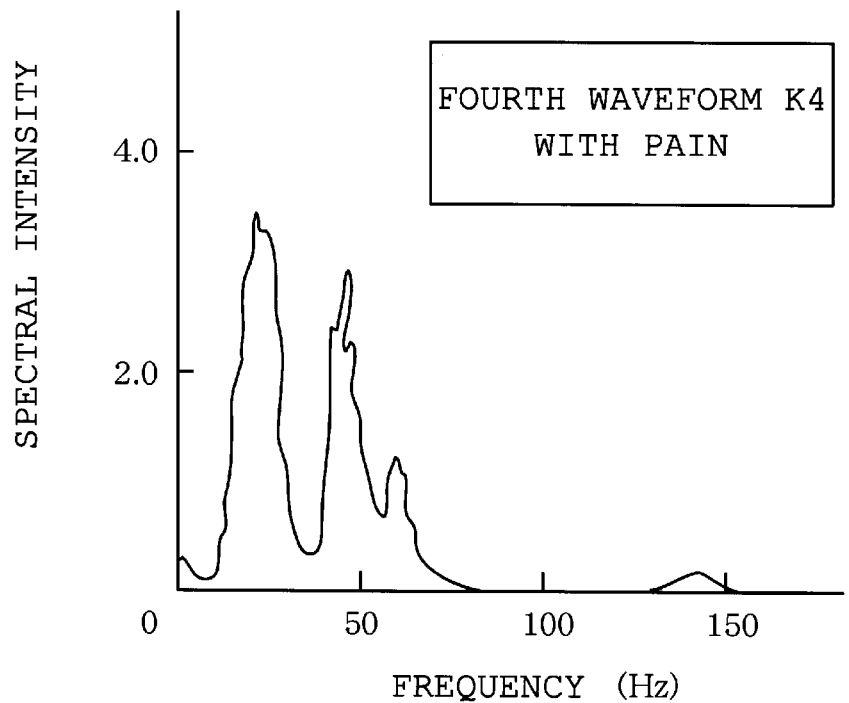
FIG. 9 is a graph which shows the Fourier transform spectrum of the fourth Korotkoff sound waveform in a condition where the specific patient feels pain.
Figure 10:
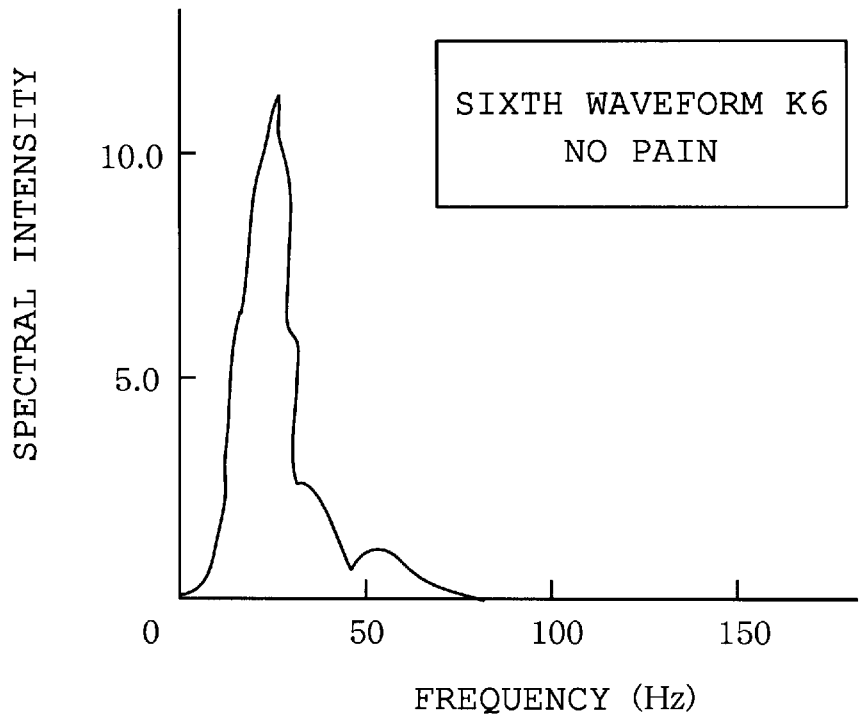
FIG. 10 is a graph which shows the Fourier transform spectrum of the sixth Korotkoff sound waveform in a condition where the specific patient feels no pain.
Figure 11:
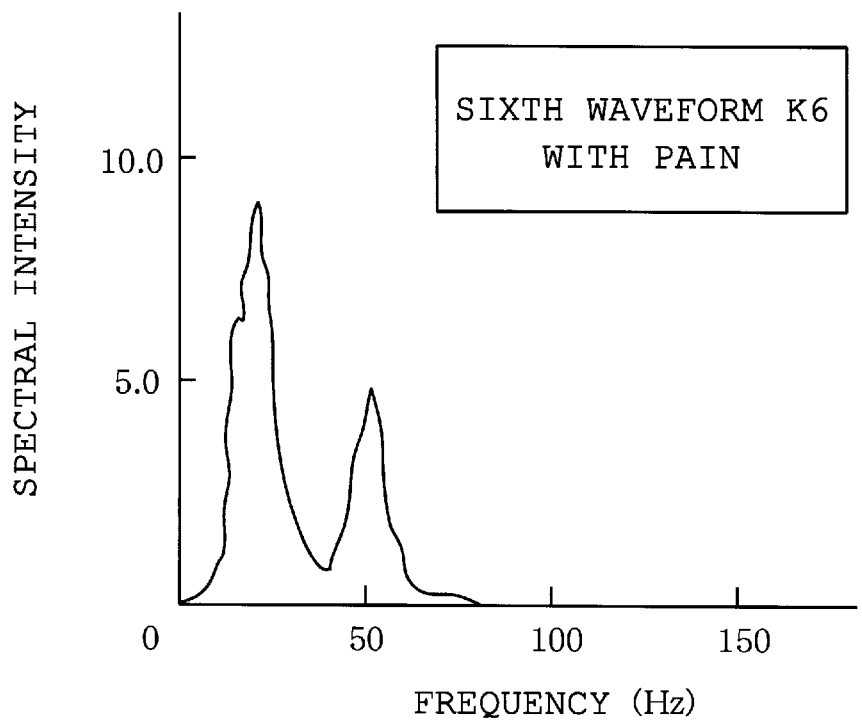
FIG. 11 is a graph which shows the Fourier transform spectrum of the sixth Korotkoff sound waveform in a condition where the specific patient feels pain.
Figure 12:
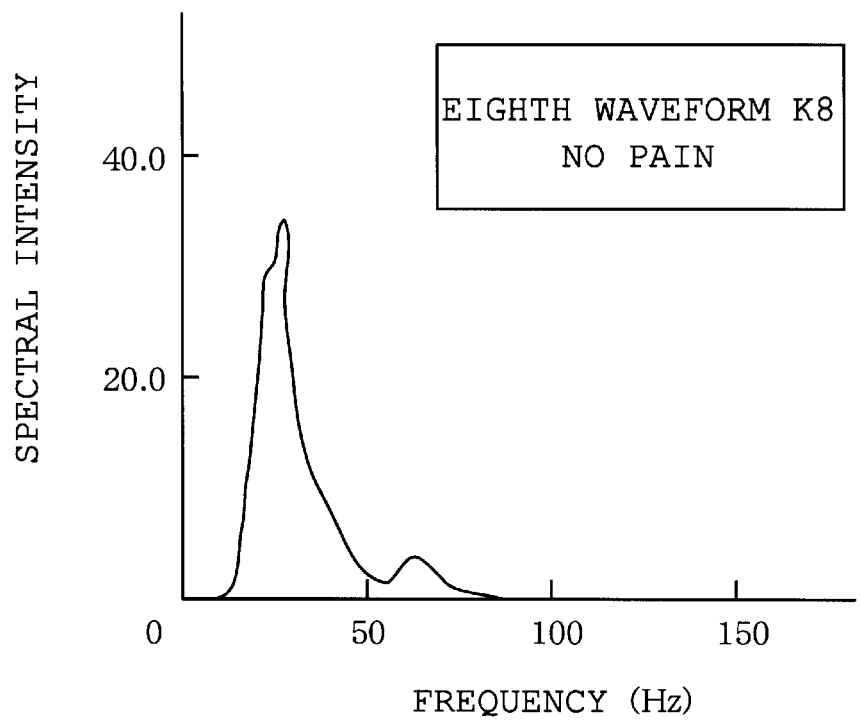
FIG. 12 is a graph which shows the Fourier transform spectrum of the eighth Korotkoff sound waveform in a condition where the specific patient feels no pain.
Figure 13:
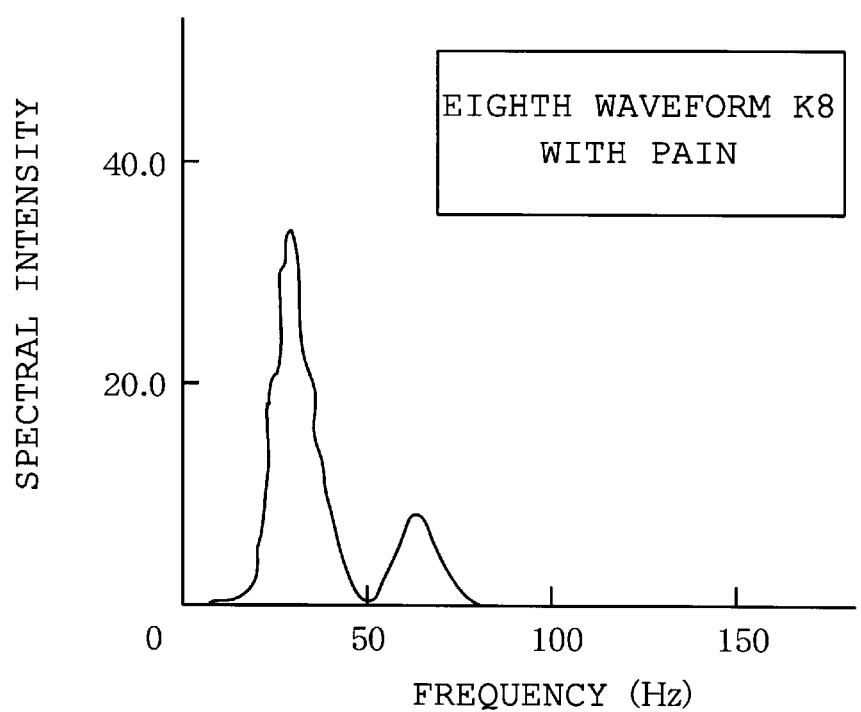
FIG. 13 is a graph which shows the Fourier transform spectrum of the eighth Korotkoff sound waveform in a condition where the specific patient feels pain.

Both FIG. 6 and FIG. 7 are graphs in which the Fourier transform results of the first waveform K1 (the Korotkoff sound waveform generated at point D) are indicated in the form of spectral waveforms. As has been mentioned above, since frequency components of 150 Hz or higher are cut out as noise components, the respective spectral waveforms only have frequency components of 150 Hz or less. Though both graphs are those for the first waveform, the spectral waveforms differ considerably from each other. This is because whereas the spectral waveform of FIG. 6 is that of a "no-pain" condition, the spectral waveform of FIG. 7 is that of a "pain" condition. It can be seen that the waveform of FIG. 7 contains numerous, steep peaks. Thus significant differences appear in the Fourier transform spectral waveforms of Korotkoff sounds depending on whether or not there is pain. This applies likewise to the fourth waveforms K4 shown in FIG. 8 and FIG. 9, the sixth waveforms K6 shown in FIG. 10 and FIG. 11, and the eighth waveforms K8 shown in FIG. 12 and FIG. 13. However, of the above-mentioned waveforms, the differences between a "no-pain" waveform and a "pain" waveform become apparent most significantly in the results of the first waveforms K1 shown in FIG. 6 and FIG. 7. The reason for this shall be discussed later.

In any case, significant differences appear in the Fourier transform spectral waveforms of Korotkoff sounds depending on whether or not there is pain, although measurements are made on the same patient, using the same device and same method. This result indicates that such spectral waveforms contain some form of pain information. At the present point, there is not enough clinical data to make a detailed analysis concerning which spectral waveforms correspond to which types of pain, etc. However, the present inventor considers, based on clinical data obtained up until now, that the number of peaks in the spectral waveform is somehow related to the type of pain. For example, it can be considered that when the number of peaks is extremely large, a piercing pain is being felt.

As far as the inventor knows, this phenomenon of pain information influencing the frequency components of Korotkoff sound has not been reported priorly. Theoretical analysis of this phenomenon has therefore has not been carried out adequately. However, the present inventor considers this phenomenon to be as follows. That is, the present inventor considers that some form of tissue vibration occurs at portions at which pain is generated and that this tissue vibration is propagated along arteries and observed via the cuff as a component of the Korotkoff sound.

With the device of the present embodiment, the Fourier transform spectral waveform of Korotkoff sound that has been measured at a desired pressure can be displayed on the screen of display device 170 and can also be printed out on paper by means of printer 180. A medical practitioner will be able to ascertain, with some degree of objectivity, the information concerning the pain that is being felt by a patient based on the spectral waveforms indicated in the above manner. For example, in the case where a spectral waveform with numerous peaks is obtained as shown in FIG. 7, a medical practitioner can assume that "the patient is feeling piercing pain." Obviously, since the entirety of the pain that is being felt by a patient cannot be grasped accurately by spectral waveforms obtained in the above manner, the medical practitioner will still have to perform the basic diagnosis of "collecting information on pain by inquiry of the patient him/herself." However, there is a great significance in being able to collect some information on pain in the form of objective data, that is, spectral waveforms.

§ 4 Relationships with the locations of pain

As shown in the graph of FIG. 5, with the device of the present embodiment, Korotkoff sound is detected at each of a plurality of pressures and the Fourier transform results of these respective Korotkoff sound waveforms are indicated. From an examination of the clinical data that the presented inventor has collected up until now, it can be assumed that each Korotkoff sound waveform mainly contains information on the pain at a location that is in correspondence to the cuff pressure at the point at which the Korotkoff sound was detected. For example, of the numerous Korotkoff sound waveforms shown in FIG. 5, the first waveform K1 mainly contains information on pain at the vicinity of the shoulder, the fourth waveform K4 mainly contains information on pain at the vicinity of the heart, the sixth waveform K6 mainly contains information on pain at the vicinity of the lungs, the eighth waveform K8 mainly contains information on pain at the vicinity of the stomach, the tenth waveform K10 mainly contains information on pain at the vicinity of the liver, the twelfth waveform K12 mainly contains information on pain at the vicinity of the kidneys, the sixteenth waveform K16 mainly contains information on pain at the vicinity of the thighs, the twenty second waveform K22 mainly contains information on pain at the vicinity of the knees, and the twenty eighth waveform K28 mainly contains information on pain at the vicinity of the periphery of the legs. The respective Korotkoff sound waveforms can thus be made to correspond to individual parts. However, specific correspondences such as the above are considered to differ among individual patients. That is, there may be such individual differences as the pain at the vicinity of the stomach appearing most significantly in the eighth waveform in one patient and appearing most significantly in the tenth waveform in another patient.

This phenomenon that information on pain at a specific location is contained in a Korotkoff waveform measured at a specific pressure can be explained by the following theory. Here, the circulatory system model illustrated in FIG. 14 shall be considered for explanation of this theory. This model shows how the blood that has been delivered from the heart passes through the arteries to be delivered to the various parts of the body. That is, a portion of the blood that has exited the heart is delivered from the shoulder part to the periphery of the hand (though only the circulatory system for the right arm is illustrated in the Figure, the same circulatory system exists for the left arm as well), another portion is delivered to the head part, and yet other portions are delivered to the lungs, stomach, liver, kidneys, thighs, periphery of the legs, etc. The heart functions as a pump that delivers blood and blood is forced into the arteries in synchronization with the heartbeat, which corresponds to the pumping action of the pump. The void arrow BF shown in FIG. 14 indicates the direction of progress of this blood flow.

Meanwhile, pressure fluctuations due to the heartbeat are propagated along the arteries as pulse waves, and it is known that when such pulse waves collide with biological tissues (which act as resistive elements that receive blood) at various parts of the body, reflected waves are generated at such parts. The arrow RW shown in FIG. 14 indicates the direction of progress of a reflected wave that proceeds towards cuff 200 that has been attached to the upper arm.

When the cuff 200 of the device of the present embodiment is attached to the upper arm, the actual blood flow, indicated by arrow BF, and the reflected wave, indicated by the arrow RW, will reach this cuff 200. In the artery under compression by cuff 200, blood 310, of an amount that corresponds to the pressure of blood flow shutting bag 210, will pass through in a cycle synchronized with the heartbeat as shown in FIG. 4. Korotkoff sound is generated during this passage of blood. Meanwhile, the time it takes for a reflected wave to reach cuff 200 will differ according to each individual reflected wave. For example, suppose that a pulse wave is generated by a heartbeat and this pulse wave is propagated to the shoulder on the one hand as well as to the periphery of the legs on the other hand. From a comparison of the time it takes for the reflected wave that is generated at the shoulder part to reach cuff 200 at the upper part and the time it takes for the reflected wave that is generated at the periphery of the legs to reach cuff 200 at the upper arm, it is obvious that, since the paths of propagation differ, the former reaching time will be shorter than the latter reaching time. That is, the reflected waves of a pulse wave that has resulted after the heart has beaten once will reach cuff 200 from the various locations of the body with differences in time. However, since a Korotkoff sound is observed only at the instant blood passes below the cuff, the observed reflected wave that is overlaid onto this Korotkoff sound will be the reflected wave that has coincidentally reached cuff 200 at the point in time of observation of the Korotkoff sound.

The average velocity of movement of blood (blood velocity) in the brachial artery is generally known to be approximately 1.5 m/sec, and if for example the distance from the heart to the upper arm is 60 cm, a Korotkoff sound will be observed approximately 0.4 seconds after blood has been discharged by a heartbeat. Meanwhile, it is known that the velocity of propagation of a pressure fluctuation (pulse wave velocity) within the aorta is approximately 4 to 5 m/sec and is thus about three times the blood velocity. If, for example, the distance from the heart to the kidneys is 60 cm, while the length of the course along which a pulse wave generated at the heart propagates through the aorta and reaches the kidneys and then a reflected wave generated at the kidneys returns to the aorta, is propagated to the brachial artery, and reaches cuff 200 at the upper arm, will be 60 cm+60 cm+60 cm=180 cm. In consideration that the propagation velocity of a pulse wave (and that of a reflected wave) is three times that of the blood velocity, the reflected wave from the kidney will reach cuff 200 about 0.4 sec after the heart has delivered the blood.

Thus if it is assumed that the distance from the heart to the cuff is 60 cm and the distance of the path that extends from the heart to the kidney and then returns towards the heart, branches off onto the brachial artery, and reaches the cuff is 180 cm, though the latter path is three times that of the former path, if the propagation velocity of a pulse wave is deemed to be three times the blood velocity, the time it takes to traverse the former path at the blood velocity will be equal to the time it takes for the latter path to be traversed at the propagation velocity of a pulse wave. Thus with the above-described model, the Korotkoff sound that is observed at the cuff will be one with which the information on the reflected wave from the kidneys is overlaid onto the information on the blood that flows below the cuff.

However, the above argument applies to conditions where the blood vessel is not compressed by a cuff. In other words, it is a phenomenon that occurs in a condition where the living body is not influenced at all by an observation system. Thus if the cuff pressure is close to the diastolic pressure DP (that is, the pressure at which the blood vessel is not compressed as shown by condition 4 of FIG. 4), the observed Korotkoff sound, in the case of the above-described model, can be considered to contain information on the reflected wave from the kidneys. However, it is known that when a blood vessel is compressed by a cuff, the blood velocity changes. That is, when pressure is applied to a blood vessel by the cuff, which is the observation system, the blood vessel diameter becomes reduced and the blood velocity at that portion increases. Though it took 0.4 sec for the blood that has been discharged from the heart to pass below the cuff with the above-described model, if for example this time is reduced to 0.3 sec due to application of pressure to the cuff, the reflected wave from the kidney will not reach the cuff at the time at which the Korotkoff sound is generated and a reflected wave from a location that is closer than the kidneys, for example, the stomach will be overlaid onto the observed Korotkoff sound.

Figure 14:
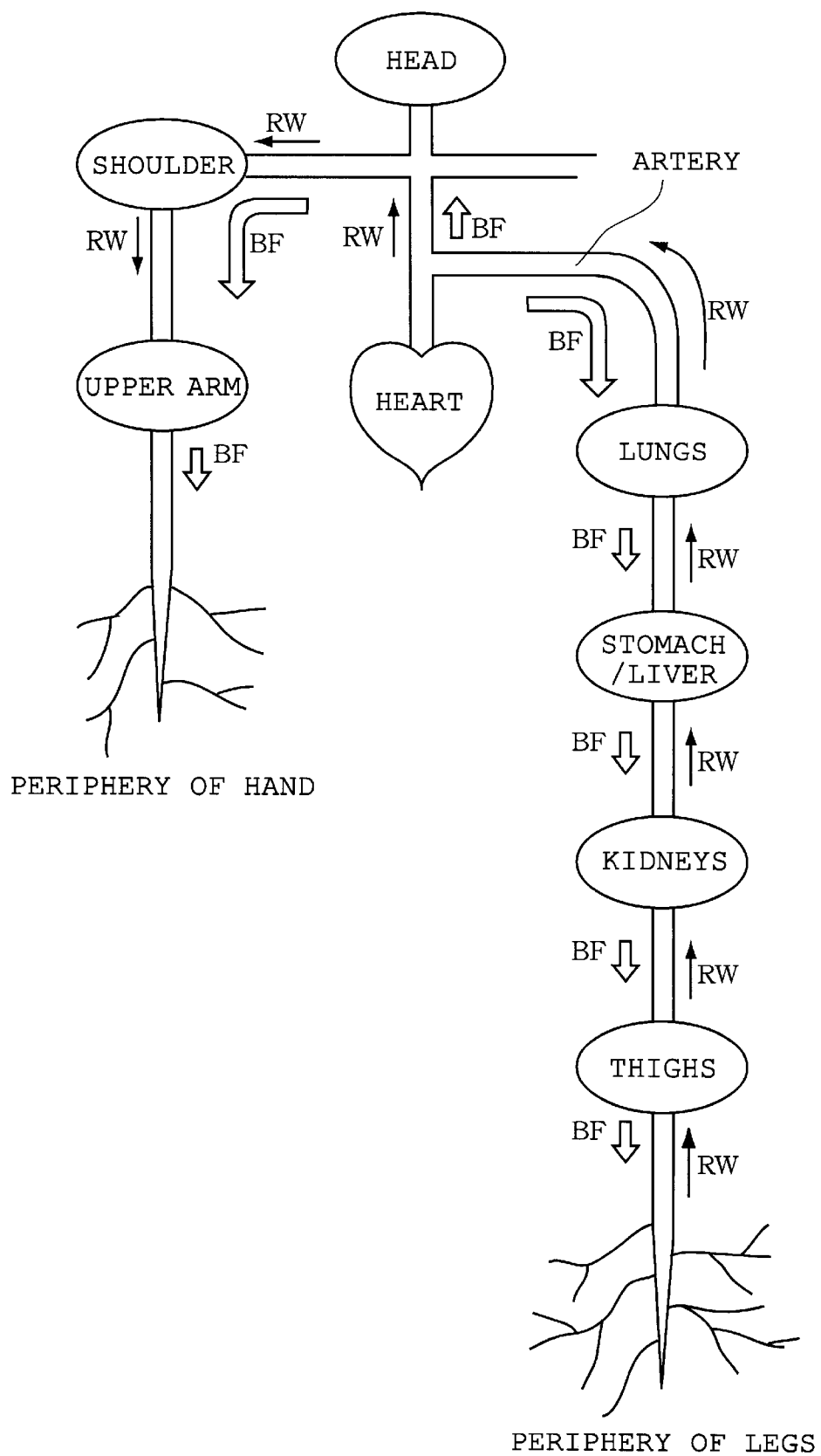
FIG. 14 is a schematic view of the portions of the human circulatory system relating to arteries.

Needless to say, since there will be differences according to individual patient's systolic pressure SP, diastolic pressure DP, blood velocity, pulse wave propagation velocity, distances from the heart to various locations, etc., the correspondence between the Korotkoff sound obtained at each cuff pressure and the location of the source of the reflected wave information that is overlaid cannot be determined uniformly. However, as shown in FIG. 14, that the path of a reflected wave along the circulatory system to the upper arm will become longer in the order of shoulder part, heart, lungs, stomach, liver, kidneys, thighs, and leg periphery will apply in common to all patients. Thus if the cuff pressure becomes lower, the reflected wave information that is contained in the Korotkoff sound will be that from a part positioned further away from the upper arm, and this will also apply in common to all patients. Thus the pressure ranges from point D to point G in the graph of FIG. 3 can be made to correspond approximately to the parts of the body in the order of shoulder part, heart, lungs, stomach, liver, kidneys, thighs, and leg periphery. Needless to say, optimal correspondences may be determined for each individual patient by taking into consideration the patient s height and the actually measured blood pressure value.

The individual spectral waveforms obtained by Fourier transform of the respective Korotkoff sounds detected at a plurality of pressures in the pressure range from point D to point G in the graph of FIG. 3 can thus be made to correspond respectively to certain parts of the body. Each spectral waveform will contain information on the reflected wave from a corresponding, specific part and will thus contain information on the pain (tissue vibration) at that part. Thus by indicating the results of Fourier transform of the respective Korotkoff sounds detected at this plurality of pressures so as to correspond respectively to specific parts of the body, clues can be provided concerning the location at which the pain is being generated.

Figure 15:
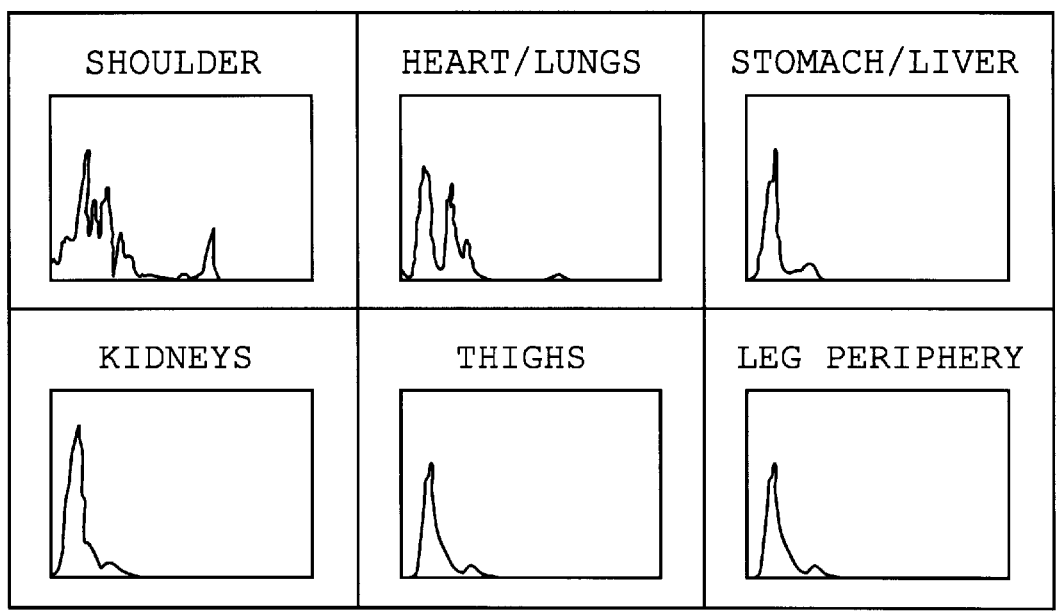
FIG. 15 is a diagram of a display screen which shows an example where the Fourier transform results for the respective Korotkoff sounds detected at a plurality of pressures are indicated in correspondence to the respective, specific parts of the body.

An example of a display on the screen of display device 170 is shown in FIG. 15. With this example, the six display areas of shoulder, heart/lungs, stomach/liver, kidneys, thighs, and leg periphery are provided and the spectral waveforms corresponding to the respective parts are displayed in the respective display areas. For example, the spectral waveform displayed at the shoulder indicates the Fourier transform result of Korotkoff sound obtained under a pressure closest to point D in the graph of FIG. 3, the spectral waveform displayed at the leg periphery indicates the Fourier transform result of Korotkoff sound obtained under a pressure closest to point G in the graph of FIG. 3. Though needless to say spectral waveforms may not be obtained for all such parts depending on the patient, the displaying of the spectral waveforms according to the respective parts will enable the location at which pain is generated to be estimated in a general manner.

That the difference between no pain and pain was most significant in the first waveform K1 shown in FIG. 6 to FIG. 7 among the measurement results shown in FIG. 6 to FIG. 13 is thus considered to be because this pain was in the shoulder and the pressure corresponding to the first waveform was the cuff pressure at which this shoulder pain appears in the Korotkoff sound. The shoulder is a special location that is extremely close to the attachment position of the cuff and all reflected waves that proceed to the cuff passes near this shoulder. The signal component that indicates pain at the shoulder will thus be overlaid to some degree on all reflected waves that proceed to the cuff. That differences between no pain and pain which appear to some degree from the fourth waveform K4 onwards in the measurement results shown in FIG. 6 to FIG. 13 are considered to be due to this reason.

§ 5 Modifications

Though the basic arrangement of the pain information detecting device by this invention has been described for one embodiment above, some modifications shall be described below.

Figure 16:
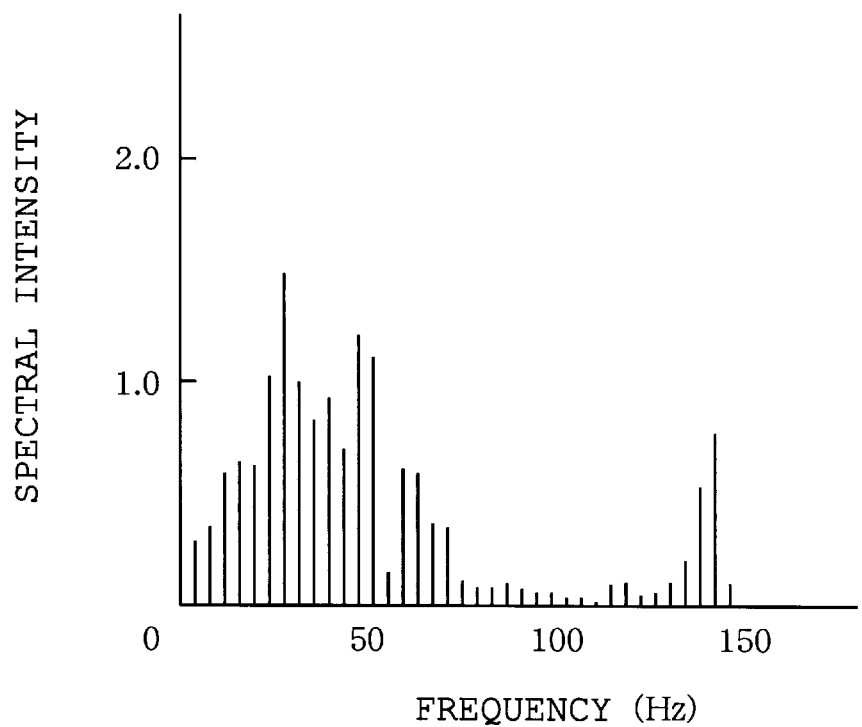
FIG. 16 is a diagram of a display screen which shows an example where the Fourier transform result is displayed as a histogram by the detecting device of FIG. 1.

First, though the Fourier transform results of Korotkoff sound were displayed as spectral waveforms in the above-described embodiment, since this invention takes note of the point that a pain signal is recognizable as a frequency distribution of the Korotkoff sound, as long as the frequency distribution of the Korotkoff sound can be indicated, the form of display may finally take on any form. For example, instead of displaying a spectral waveform, the spectral intensity values of components contained within a specific frequency range may be displayed as a histogram. FIG. 16 shows a display example of such a histogram. However since spectral peaks can be recognized directly with a spectral waveform, the above-described display by a spectral waveform is more preferable.

Figure 17:
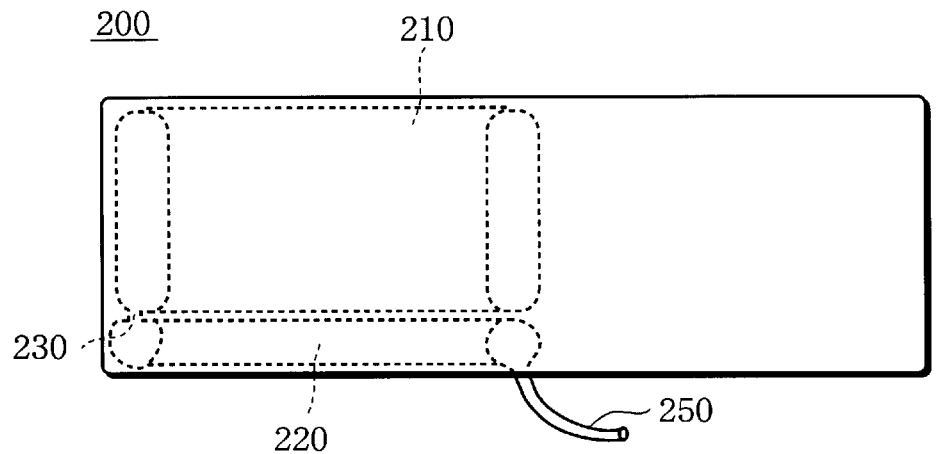
FIG. 17 is a plan view of a modification of a cuff that can be used in the detecting device of FIG. 1.
Figure 18:
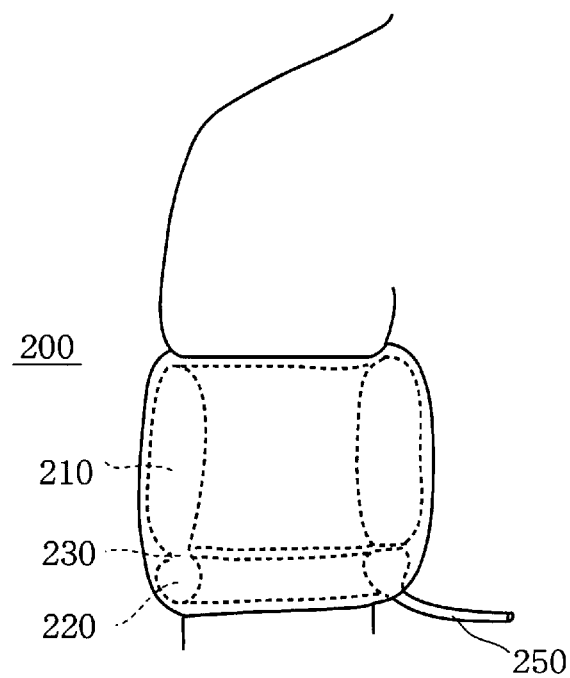
FIG. 18 is a diagram which shows the condition where the cuff of FIG. 17 is attached to an upper arm.

The cuff 200 shown in FIG. 1 is that of a basic form that can be used in this invention, and as long as the measurement of Korotkoff sound is enabled, a cuff of any form may be used. For example, the cuff 200 shown in FIG. 17 has a blood flow shutting bag 210 and a detection bag 220 and these two parts are interconnected by a connection path 230 as in the cuff 200 shown in FIG. 1. However, a duct is not provided directly on blood flow shutting bag 210. The duct 250, which extends to main device unit 100 is connected only at the detection bag 220 side, and pressure control of the cuff and Korotkoff sound detection are all performed via this duct 250. FIG. 18 is a diagram which shows the condition where this cuff has been attached to an upper arm.

Needless to say, a cuff having a plurality of bags does not have to be used, and a cuff having just a blood flow shutting bag may be used instead. However, since a blood flow shutting bag must have an adequate volume to stop the blood flow in an artery, the waveform of Korotkoff sound that is detected by a blood flow shutting bag may be distorted considerably. Thus for practical purposes, it is preferable to provide a detection bag that is smaller in volume than a blood flow shutting bag and to detect the Korotkoff sound with this detection bag.

Also, though with the embodiment shown in FIG. 1, the necessary control devices and computation devices are all housed inside main device unit 100, a part of these may be realized by an external personal computer, etc. For example, the CPU 130 housed inside main device unit 100 may be arranged to perform just the pressure control and the collection of Korotkoff sound data and an externally connected personal computer may be made to perform the Fourier transform process, the spectral waveform indication process, etc. In this case, the spectral waveform may be displayed on the display screen of a personal computer and may be printed out from a printer connected to the personal computer.

INDUSTRIAL APPLICABILITY

Though the pain information detecting device of the present invention does not necessarily have the function of accurately detecting the pain a patient is feeling, since it can indicate information related to pain in the form of spectral waveforms, it enables provision of data that can serve as material for diagnosis. Until now, the collection of information concerning pain largely depended on the chief complaints or inquiry of a patient. By using the device of this invention, objective data concerning pain can be obtained simply by attaching a cuff to an upper arm of a patient. The device of this invention can therefore be put to use in diagnosis in various medical fields.

What is claimed is:

1. A pain information detecting device comprising:
    a cuff (200), having a blood flow shutting bag (210) for shutting the blood flow through an artery;
    a pressure control device (120, 130, 140, 150) for controlling the pressure of said blood flow shutting bag;
    a sound wave sensor (110) for detecting the Korotkoff sound that is generated when blood flows through an artery under compression by said blood flow shutting bag;
    a computation device (130) which performs Fourier transform of signals of the Korotkoff sound detected by said sound wave sensor; and
    an indication device (170, 180), which indicates the results of said Fourier transform as pain information.

2. A pain information detecting device as set forth in claim 1, wherein:
    the cuff is provided with a detection bag (220) which is partially interconnected with the blood flow shutting bag and is smaller in volume than the blood flow shutting bag, and the sound wave sensor (110) detects the Korotkoff sound based on pressure fluctuations inside said detection bag.

3. A pain information detecting device as set forth in claim 1, wherein:
    the computation device (130) has a function of indicating pain information on the indication device (170, 180) by cutting off components of a prescribed frequency or higher after performing the Fourier transform.

4. A pain information detecting device as set forth in claim 1, wherein:
    the computation device (130) has a function of making the indication device (170, 180) indicate the Fourier transform result in a form of a spectral waveform or a histogram.

5. A pain information detecting device as set forth in claim 1, wherein:

the pressure control device (120, 130, 140, 150) has a function of controlling the pressure of the blood flow shutting bag to gradually decrease from a pressure high enough to stop blood flow, so that results of Fourier transform of respective Korotkoff sounds detected for a plurality of pressures are made to be indicated on the indication device (170, 180).

6. A pain information detecting device as set forth in claim 5, wherein:

results of Fourier transform of respective Korotkoff sounds detected for a plurality of pressures are respectively made to be indicated in correspondence to specific parts of human body.

* * * * *